United States Patent [19]

Rigterink et al.

[11] Patent Number: 4,536,341

[45] Date of Patent: Aug. 20, 1985

[54] SUBSTITUTED N-AROYL N'-PHENYL UREA COMPOUNDS

[75] Inventors: Raymond H. Rigterink, Midland, Mich.; Ronald J. Sbragia, Clayton, Calif.

[73] Assignee: The Dow Chemical Company, Midland, Mich.

[21] Appl. No.: 520,033

[22] Filed: Aug. 3, 1983

Related U.S. Application Data

[62] Division of Ser. No. 401,491, Jul. 26, 1982, Pat. No. 4,468,405.

[51] Int. Cl.$^3$ .................. C07C 157/09; C07C 122/00; C07C 127/19

[52] U.S. Cl. ............... 260/453 AR; 260/454; 260/453 A; 564/26; 564/52; 564/442; 564/443; 564/440; 564/28; 564/29; 564/48; 564/49; 564/53; 564/54

[58] Field of Search ............ 260/454, 453 AR, 453 A; 564/26, 52, 442, 443, 440, 28, 29, 48, 49, 53, 54

[56] References Cited

U.S. PATENT DOCUMENTS 4,284,628 8/1981 Nakagawa et al. ................. 260/454

Primary Examiner—Henry R. Jiles
Assistant Examiner—Robert C. Whittenbaugh

[57] ABSTRACT

Dihalo and haloalkyl, haloalkoxy or haloalkylthio-substituted anilines and aniline derivatives, e.g. isocyanates that are useful in the preparation of acyl ureas having insecticidal activity.

5 Claims, No Drawings

SUBSTITUTED N-AROYL N'-PHENYL UREA COMPOUNDS

CROSS-REFERENCE TO RELATED APPLICATION

This is a divisional of application Ser. No. 401,491 filed July 26, 1982, now U.S. Pat. No. 4,468,405.

BACKGROUND OF THE INVENTION

This invention relates to novel substituted N-aroyl N'-phenyl ureas, a process for producing them, insecticidal compositions containing them and a method for controlling certain insects.

Various insecticidal derivatives of urea are known in the art, such as, for example, U.S. Pat. Nos. 4,173,638; 4,005,223; 4,170,657; 4,139,636; 4,089,975 and German Patent Application No. 3,003,113.

The N-aroyl N'-phenyl ureas of the present invention are more active and have a broader spectrum of effectiveness than the benzoylurea insecticides currently available.

SUMMARY OF THE INVENTION

The novel compounds of this invention are N-aroyl N'-phenyl ureas having the formula

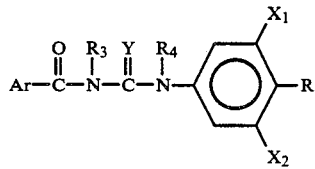

wherein Ar is a substituted phenyl, pyridyl or pyrimidinyl radical wherein the substituents are chloro, bromo, fluoro, $C_1-C_3$ alkyl or $C_1-C_3$ alkoxy, with the proviso that at least one substituent is positioned ortho to the carbonyl group; $R_3$ and $R_4$ are individually H or $C_1-C_4$ alkyl or together they form the group

Y is O or S; $X_1$ and $X_2$ are halogen, and R is a $C_1-C_4$ haloalkyl, haloalkoxy or haloalkylthio group.

These novel compounds can be prepared by methods analogous to those known in the art, e.g., as taught in U.S. Pat. No. 4,139,636.

The invention also provides insecticidal compositions comprising an insecticidally effective amount of the above described N-aroyl N'-phenyl ureas in admixture with a suitable carrier or adjuvant therefore and a method for killing and/or controlling insects which comprises applying the active compound, alone or in admixture with a carrier, to the insects, the insect larvae or their habitats.

DETAILED DESCRIPTION OF THE INVENTION

The preferred compounds of this invention are those having the formula

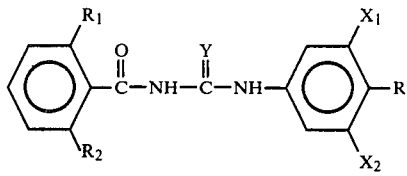

where $R_1$ is F or Cl; $R_2$ is F, Cl or H; Y is O or S; $X_1$ and $X_2$ are halogen and R is $OCF_3$, $OCF_2CHF_2$, $OCF_2CHClF$, $OCF_2CFHBr$ or $OCF_2CHCl_2$. Most preferably, $R_1$ is F or Cl $R_2$ is F, $X_1$ and $X_2$ are chlorine and R is $OCF_2$CHClF, $OCF_2CHF_2$ or $OCF_2CHFBr$.

The compounds of the present invention are normally crystalline solids of low solubility in water and of moderate solubility in many organic solvents. The compounds have low phytotoxicity and have exceptional activity in the control of various undesirable agricultural, household and veterinary insect pests.

Representative of the various insects which can be controlled by the active compounds of the present invention are members of the orders Lepidoptera, Coleoptera, Diptera, Orthoptera, Homoptera, Thysanoptera and Acarina. They are active against normally sensitive and resistant species at some stages of development. Examples of insect pests comprising the above include the tobacco budworm (*Heliothis virescens*), the beet armyworm (*Spodoptera exigua*), the Egyptian cotton leafworm (*Spodoptera littoralis*), the American bollworm (*Heliothis armigera*), the diamond-back moth (*Plutella maculipennis*), the gypsy moth (*Lymantria dispar*), the cutworm (*Agrotis segetum*), the Mediteranean flour moth (*Ephestia kuehniella*), the Colorado potato beetle (*Leptinotarsa decimlineata*), the mustard beetle (*Phaedon cochleariae*), the cottom boll weevil (*Anthonomus grandis*), the Mexican bean bettle (*Epilachna varivestis*), the khapra beetle (*Trogoderma granarium*), the housefly (*Musca domestica*), the lesser housefly (*Fannia canicularis*), the Mediterranean fruit fly (*Ceratitis capitata*), the black blow fly (*Phormia regina*), the cabbage rootfly (*Hylemya brassicae*), the yellow fever mosquito (*Aedes aegypti*), the malaria mosquito (*Anopheles stephensi*), the desert locust (*Schistocerca gregaria*), the migratory locust (*Locusta migratoria*), the German cockroach (*Blattells germanica*), the American cockroach (*Periplaneta americana*), the pear psylla (*Psylla pyricola*), the onion thrips (*Thrips tabaci*), and the citrus rust mite (*Phyllocoptruta oleivora*).

The compounds are highly active and can be employed to kill insects outright and/or to prevent adult emergence from juvenile forms of the insect. In such applications, the insect to be controlled and/or its habitat is contacted or treated with an insecticidal amount of one or more of the compounds of the present invention. The compounds may be administered orally to warm blooded animals from which they are excreted unchanged and they effectively combat the larvae of certain feces inhabiting insects, e.g., the face fly, horn fly and buffalo fly.

For all such uses, these compounds can be employed in unmodified form. However, the present invention embraces the use of an insecticidally-effective amount of the active ingredients in composition form with a material known in the art as an adjuvant or carrier.

Thus, for example, compositions employing one or a combination of these active ingredients can be in the form of a liquid or a dust; and the adjuvant employed can be any one of a plurality of materials including aromatic solvents, petroleum distillates, water or other liquid carriers, propellant substances, surface-active dispersing agents, light absorbers and finely-divided carrier solids.

The exact concentration of one or a combination of the compounds of the present invention in a composition thereof with an adjuvant therefore can vary; it is only necessary that one or a combination of the compounds be present in a sufficient amount so as to make possible the application of an insecticidally-effective or inactivating dosage.

Generally, for practical applications, one or a combination of these active ingredients can be broadly applied to the insect larvae or their habitat in compositions containing from about 0.0001 to about 98 percent by weight, preferably 5 to 50 percent by weight, of the compounds.

The invention is further illustrated by the following examples.

EXAMPLE 1

3,5-Dichloro-4-(2,2-dichloro-1,1-difluoroethoxy)phenyl isocynate 3,5-Dichloro-4-(2,2-dichloro-1,1-difluoroethoxy)benzenamine (12 g, 0.04 mole) was added to a solution of 20 g oxalyl chloride in 100 ml CCl$_4$ and heated under reflux with stirring for 0.5 hour. A solid precipitated. The carbon tetrachloride and excess oxalyl chloride were removed by evaporation in a rotary evaporator. The residue (16 g) was a slightly oily white solid, which was used in the next reaction without purification.

EXAMPLE 2

N-(((3,5-Dichloro-4-(2,2-dichloro-1,1-difluoroethoxy)-phenyl)amino)carbonyl)-2-chloro-3-pyridinecarboxamide

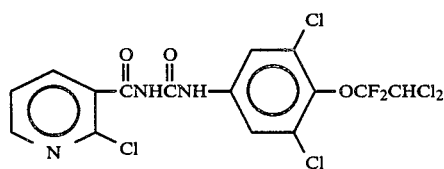

2-Chloro-3-pyridinecarboxamide (6.3 g, 0.04 mole) and 3,5-dichloro-4-(2,2-dichloro-1,1-dichloroethoxy)-phenyl isocyanate (crude; 16 g, 0.04 mole) were added to 250 ml xylene and heated under reflux with stirring for two hours. After cooling in ice water, the precipitated product was removed by suction filtration. This was recovered as 2-chloro-3-pyridine carboxamide. A second crop was obtained by adding about 400 ml hexane to the filtrate. The second crop was a mixture of the desired material and recovered amide. The desired material was isolated and purified by recrystallizing twice from toluene. M.P.=189°-192° C. NMR spectral features supported the structural assignment.

EXAMPLE 3

N-(((3,5-Dichloro-4-(2,2-dichloro-1,1-difluoroethoxy)-phenyl)amino)carbonyl)-2,6-difluoro-N-methylbenzamide

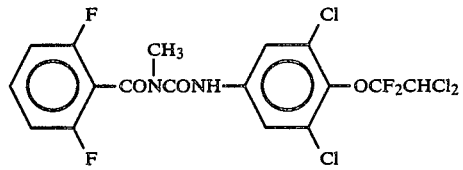

N-(((3,5-Dichloro-4-(2,2-dichloro-1,1-difluoroethoxy)phenyl)amino)carbonyl)-2,6-difluorobenzamide (9.9 g, 0.02 mole) and KOH (1.4 g, 87 percent purity, 0.02 mole) were added to 50 ml dimethylformamide with stirring, giving a clear solution. Iodomethane (3.2 g, 0.022 mole) was added and the resulting solution was stirred at room temperature for about 24 hours. The precipitated product was collected by suction filtration and dried. The product was purified by recrystallization from isopropanol. The purified product was a white solid melting at 153°-155° C. NMR spectral features support the structural assignment.

Elemental Analysis: Calcd: C, 40.18; H, 1.98; N, 5.51. Found: C, 40.3; H, 2.10; N, 5.43.

EXAMPLE 4

N-(((3,5-Dichloro-4-(2-chloro-1,1,2-trifluoroethoxy)-phenyl)amino)carbonyl)-2,6-difluorobenzamide

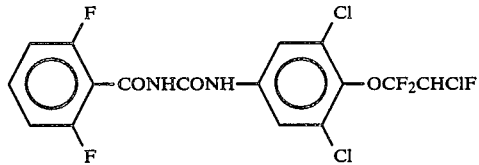

2,6-Difluorobenzoyl isocyanate (5.5 g, 0.03 mole) was added to a solution of 3,5-dichloro-4-(2-chloro-1,1,2-trifluoroethoxy)benzenamine (8.8 g, 0.03 mole) in 150 ml toluene and heated under reflux with stirring for one hour giving a clear solution. Toluene was removed by evaporation in a rotary evaporator. The residue was recrystallized from aqueous acetic acid and then from acetonitrile giving a white solid (8.3 g, 58 percent yield), melting at 178°-180° C.

Elemental analysis: Calcd: C, 40.23; H, 1.69; N, 5.87. Found: C, 40.20; H, 1.79; N, 5.83.

Employing the above procedures and appropriate starting materials, the following compounds were prepared:

N-(((3,5-Dichloro-4-(1,1,2,2-tetrafluoroethoxy)-phenyl)amino)carbonyl)-3,5-dichloro-4-pyridinecarboxamide.

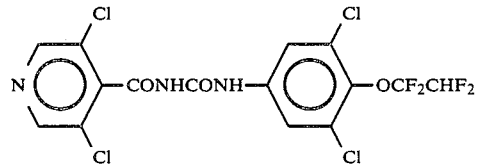

M.P.=217°-219° C.

N-(((3,5-dichloro-4-(1,1,2,2-tetrafluoroethoxy)phenyl-)amino)carbonyl)-2,6-difluorobenzamide.

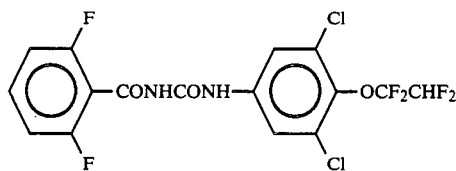

M.P.=197°-199° C.
Analysis: Calcd: C, 41.67; H, 1.75; N, 6.08. Found: C, 41.8; H, 1.92; N, 6.06.
N-(((3,5-dichloro-4-(1,1,2,2-tetrafluoroethoxy)phenyl-)amine)carbonyl)-2-chlorobenzamide.

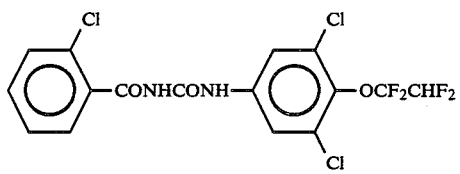

M.P.=173°-175° C.
Analysis: Calcd: N, 6.10. Found: N, 6.34.
3,5-Dichloro-N-(((3,5-dichloro-4-(2,2-dichloro-1,1-difluoroethoxy)phenyl)amino)carbonyl)-4-pyridinecarboxamide.

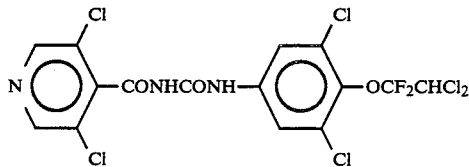

M.P.=228°-230° C.
N-(((3,5-Dichloro-4-(2,2-dichloro-1,1-difluoroethoxy)-phenyl)amino)carbonyl)-2-methoxybenzamide.

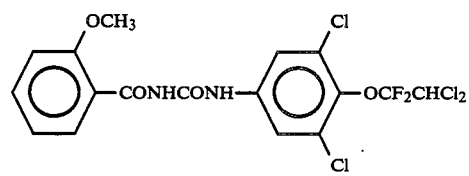

M.P.=156°-158° C.
Analysis: Calcd: 41.83% C; 2.48% H; 5.74% N. Found: 41.9% C; 2.57% H; 5.92% N.
N-(((3,5-Dichloro-4-(2,2-dichloro-1,1-difluoroethoxy)-phenyl)amino)carboxyl)-2,6-difluorobenzamide.

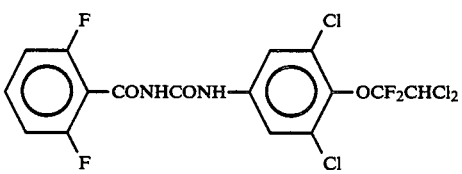

M.P.=199°-201° C.
Analysis: Calcd: N, 5,67. Found: N, 5.66.
2-Chloro-N-(((3,5-dichloro-4-(2,2-dichloro-1,1-difluoroethoxy)phenyl)amino)carbonyl)benzamide.

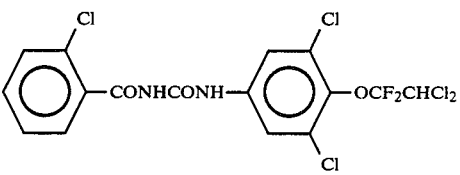

M.P.=200°-202° C.
Analysis: Calcd: N, 5.69. Found: N, 5.60.

In addition to the above described preparative methods, many of the compounds of this invention can be made by reacting a compound having the formula

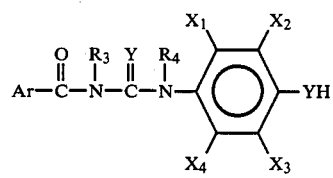

wherein all of the substituents are as above defined, with a haloalkene as is known in the art.

The biological activity of several of these compounds was determined. In the beet armyworm test, cotton leaves were dipped in aqueous suspensions of the chemicals, dried, excised and placed into petri dishes with five second-instar beet armyworm (*Spodoptera exigua*) larvae. Mortality counts were made five days later. The tobacco budworm test was the same except that five tobacco budworm (*Heliothis virescens*) larvae were placed onto the treated leaves. The results are summarized below:

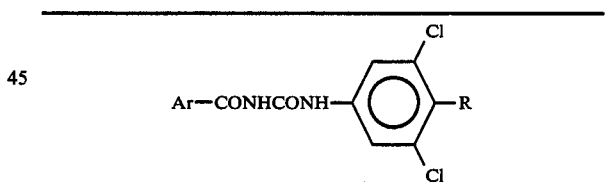

| Compound | Ar | R |
|---|---|---|
| A | 2,6-difluorophenyl | $OCF_2CHCl_2$ |
| B | 2-chlorophenyl | $OCF_2CHCl_2$ |

| | Percent Control at Indicated Dosage, ppm | | | | | |
|---|---|---|---|---|---|---|
| | Beet Army Worm Test (1) | | | Tobacco Budworm Test (2) | | |
| Compound | 400 | 100 | 25 | 400 | 100 | 25 |
| A | 100 | 100 | 100 | 100 | 100 | 80 |
| B | 100 | 100 | 100 | 100 | 80 | 40 |

(1) Untreated check mortality 0%.
(2) Untreated check mortality 27%.

Employing the above described preparative and testing methods, the compounds listed in the following table were prepared and tested. The test results, $LD_{90}$ ppm, indicate the dosage necessary to obtain 90 percent kill of the indicated insect.

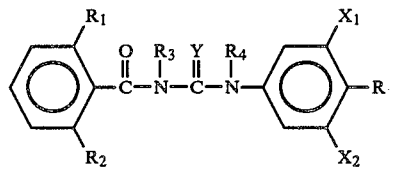

| Ex. No. | $R_1$ | $R_2$ | $R_3$ | $R_4$ | Y | $X_1$ | $X_2$ | R | Melting Point °C. | LD$_{90}$, ppm Beet Army-worm | LD$_{90}$, ppm Tobacco Budworm |
|---|---|---|---|---|---|---|---|---|---|---|---|
| 1 | F | F | H | H | O | Cl | Cl | OCF$_2$CHF$_2$ | 204–206 | 1.6 | 1.6 |
| 2 | F | F | H | H | O | Cl | Cl | OCF$_2$CHFCl | 176–178 | 1.2 | 1.2 |
| 3 | F | F | H | H | O | Cl | Cl | OCF$_2$CHFBr | 170–172 | 1.2 | 2.5 |
| 4 | F | F | H | H | O | Cl | Cl | OCF$_2$CHFI | 170–172 | | 12.5 |
| 5 | F | F | H | H | O | Cl | Cl | OCF$_2$CHCl$_2$ | 180–182 | 5.0 | 25.0 |
| 6 | F | F | H | H | O | Cl | Cl | OCF$_2$CH$_2$Cl | 188–190 | 100.0 | 100.0 |
| 7 | F | F | H | H | O | Cl | Cl | OCF$_2$CHBr$_2$ | 215–217 | 25.0 | 400.0 |
| 8 | F | F | H | H | O | Cl | Cl | OCFClCHFCl | 203–205 | 1.25 | 25.0 |
| 9 | F | F | H | H | O | Cl | Cl | OCF$_3$ | 218–220 | 0.6 | 12.5 |
| 10 | F | F | H | H | O | Cl | Cl | OCF$_2$CF$_3$ | 224–227 | 12.5 | 50.0 |
| 11 | F | F | H | H | O | Cl | Cl | SCF$_2$CHFCl | 250–260 | 200.0 | >400.0 |
| 12 | F | F | H | H | O | Cl | Cl | SCF$_2$CHF$_2$ | 166–168 | 3.1 | 12.5 |
| 13 | Cl | H | H | H | O | Cl | Cl | OCF$_2$CHFCl | 178–180 | 5.0 | 6.2 |
| 14 | Cl | H | H | H | O | Cl | Cl | OCF$_2$CHF$_2$ | 173–175 | 100.0 | 25.0 |
| 15 | Cl | H | H | H | O | Cl | Cl | OCF$_2$CHFBr | 183–185 | 2.5 | 10.0 |
| 16 | Cl | H | H | H | O | Cl | Cl | OCF$_2$CHFI | 171–174 | | 50.0 |
| 17 | Cl | H | H | H | O | Cl | Cl | OCF$_2$CHCl$_2$ | 162–164 | 6.2 | 200.0 |
| 18 | Cl | H | H | H | O | Cl | Cl | OCF$_2$CHBr$_2$ | 217–219 | 25.0 | 400.0 |
| 19 | Cl | H | H | H | O | Cl | Cl | OCF$_3$ | 203–205 | 2.5 | 12.5 |
| 20 | Cl | H | H | H | S | Cl | Cl | OCF$_2$CHFCl | 137–139 | 10.0 | 200.0 |
| 21 | Cl | H | H | H | S | Cl | Cl | OCF$_2$CHF$_2$ | 140–142 | 400.0 | 50.0 |
| 22 | F | F | H | H | S | Cl | Cl | OCF$_2$CHFCl | 149–151 | 12.5 | 12.5 |
| 23 | F | F | H | H | S | Cl | Cl | OCF$_2$CHF$_2$ | | | |
| 24 | F | H | H | H | O | Cl | Cl | SCF$_2$CHFCl | 245–250 | >400.0 | >400.0 |
| 25 | F | H | H | H | O | Cl | Cl | OCF$_2$CHFCl | 165–167 | 100.0 | 25.0 |
| 26 | F | Cl | H | H | O | Cl | Cl | OCF$_2$CHF$_2$ | | | |
| 27 | F | Cl | H | H | O | Cl | Cl | OCF$_2$CHFCl | 205–207 | 2.5 | 5.0 |
| 28 | F | Cl | H | H | O | Cl | Cl | OCF$_2$CHFBr | 184–186 | 2.5 | 5.0 |
| 29 | Cl | Cl | H | H | O | Cl | Cl | OCF$_2$CHF$_2$ | 217–219 | 25.0 | 25.0 |
| 30 | Cl | Cl | H | H | O | Cl | Cl | OCF$_2$CHFCl | 221–223 | 6.2 | 25.0 |
| 31 | Cl | Cl | H | H | O | Cl | Cl | OCF$_2$CHFBr | 200–202 | 100.0 | 12.5 |
| 32 | Cl | Cl | H | H | O | Cl | Cl | SCF$_2$CHF$_2$ | 213–215 | 50.0 | 200.0 |
| 33 | F | F | CH$_3$ | H | O | Cl | Cl | OCF$_2$CHCl$_2$ | 153–155 | 100.0 | >400.0 |
| 34 | F | F | CH$_3$ | H | O | Cl | Cl | OCF$_2$CHFCl | 128–130 | 100.0 | 50.0 |
| 35 | F | F | CH$_3$ | H | O | Cl | Cl | OCF$_2$CHF$_2$ | 102–104 | 100.0 | 50.0 |
| 36 | F | F | −C(=O)−C(=O)− | | O | Cl | Cl | OCF$_2$CHCl$_2$ | 194–197 | 400.0 | >400.0 |
| 37 | F | F | −C(=O)−C(=O)− | | O | Cl | Cl | OCF$_2$CHF$_2$ | 166–169 | 100.0 | >400.0 |
| 38 | F | F | −C(=O)−C(=O)− | | O | Cl | Cl | OCF$_2$CHFCl | 190–192 | 400.0 | 400.0 |
| 39 | F | F | H | H | O | Br | Br | OCF$_2$CHF$_2$ | 201–203 | 3.7 | 10.0 |
| 40 | CH$_3$ | H | H | H | O | Cl | Cl | OCF$_2$CHFCl | 163–165 | | >200.0 |
| 41 | CH$_3$ | CH$_3$ | H | H | O | Cl | Cl | OCF$_2$CHFCl | 175–177 | | 200.0 |
| 42 | C$_2$H$_5$ | C$_2$H$_5$ | H | H | O | Cl | Cl | OCF$_2$CHFCl | 182–184 | 100.0 | 400.0 |
| 43 | OCH$_3$ | H | H | H | O | Cl | Cl | OCF$_2$CHCl$_2$ | 156–158 | >400.0 | >400.0 |
| 44 | OCH$_3$ | OCH$_3$ | H | H | O | Cl | Cl | OCF$_2$CHFCl | 203–206 | 100.0 | 25.0 |
| 45 | OCH(CH$_3$)$_2$ | H | H | H | O | Cl | Cl | OCF$_2$CHFCl | 239–241 | >400.0 | >400.0 |
| 46 | OCH(CH$_3$)$_2$ | H | H | H | O | Cl | Cl | OCF$_2$CHF$_2$ | 242–244 | >400.0 | >400.0 |

$$\underset{\text{Ar}}{\text{Ar}}-\overset{\overset{O}{\|}}{C}-NH-\overset{\overset{O}{\|}}{C}NH-\underset{\underset{Cl}{|}}{\overset{\overset{Cl}{|}}{\underset{\phantom{|}}{\bigcirc}}}-R$$

| Ar | R | M.P., °C. | LD$_{90}$, ppm Beet Armyworm | Tobacco Budworm |
|---|---|---|---|---|
| 2-Cl-pyridin-3-yl | OCF$_2$CHCl$_2$ | 189–192 | 100 | >400 |
| 2,6-diCl-pyridin-3-yl | OCF$_2$CHF$_2$ | 217–219 | >400 | >400 |
| 2,6-diCl-pyridin-3-yl | OCF$_2$CHCl$_2$ | 228–230 | >400 | >400 |

In further embodiments, the compounds of the present invention or compositions containing the same, can be advantageously employed in combination with one or more additional pesticidal compounds. Such additional pesticidal compounds may be insecticides, nematocides, acaricides, herbicides, fungicides or bactericides that are compatible with the compounds of the present invention in the medium selected for application and not antagonistic to the activity of the present compounds. Accordingly, in such embodiments the pesticidal compound is employed as a supplemental toxicant for the same or for a different pesticidal use, or as an additament. The compounds in combination can generally be present in the ratio of from 1 to 100 parts of the compound of the present invention with from 100 to 1 parts of the additional compound(s).

The compounds of this invention are, or tend to be, slow acting, i.e., they disrupt the molting of the insect, thereby killing it. As a result, some time can pass before the insects are killed. Accordingly, an increased benefit can be obtained by combining the compounds of this invention with quicker acting insecticides such as, for example organophosphorus compounds, carbamates and pyrethroids. Because of this different mode of action, the compounds of this invention kill or control insects which have, or may be developing, resistance to the more common insecticides and thus they inhibit or delay the development of resistance to such insecticides.

Various modifications may be made in the present invention without departing from the spirit or scope thereof and it is understood that we limit ourselves only as defined in the appended claims.

We claim:

1. A compound having the formula

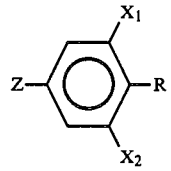

wherein $X_1$ and $X_2$ are halogen which may be the same or different, R is a $C_1$-$C_4$ haloloweralkyl, haloloweralkoxy or haloloweralkylthio group and Z is NH$_2$, —N=C=O,

$-NH-\overset{\overset{O}{\|}}{C}-NH_2$, N=C=S or $-NH-\overset{\overset{S}{\|}}{C}-NH_2$.

2. Compound of claim 1 wherein $X_1$ and $X_2$ are independently F, Cl or Br and R is OCF$_3$, OCF$_2$CHCl$_2$, OCF$_2$CHF$_2$, OCF$_2$CHFCl or OCF$_2$CHFBr.

3. Compound of claim 2 wherein $X_1$ and $X_2$ are both Cl and R is OCF$_2$CHF$_2$.

4. Compound of claim 2 wherein $X_1$ and $X_2$ are both Cl and R is OCF$_2$CHFCl.

5. Compound of claim 2 wherein $X_1$ and $X_2$ are both Cl and R is OCF$_2$CHFBr.

* * * * *

REEXAMINATION CERTIFICATE (905th)

United States Patent [19]

Rigterink et al.

[11] B1 4,536,341

[45] Certificate Issued Jul. 26, 1988

[54] SUBSTITUTED N-AROYL N-PHENYL UREA COMPOUNDS

[75] Inventors: Raymond H. Rigterink, Midland, Mich.; Ronald J. Sbragia, Clayton, Calif.

[73] Assignee: The Dow Chemical Company, Midland, Mich.

Reexamination Request:
No. 90/001,143, Dec. 22, 1986

Reexamination Certificate for:
Patent No.: 4,536,341
Issued: Aug. 20, 1985
Appl. No.: 520,033
Filed: Aug. 3, 1983

Related U.S. Application Data

[62] Division of Ser. No. 401,491, Jul. 26, 1982, Pat. No. 4,468,405.

[51] Int. Cl.$^4$ ............... C07C 119/048; C07C 127/22; C07C 153/057; C07C 157/12

[52] U.S. Cl. ............................ 558/13; 560/358; 564/23; 564/26; 564/28; 564/29; 564/44; 564/48; 564/49; 564/52; 564/53; 564/54; 564/440; 564/442; 564/443

[58] Field of Search ............... 560/358; 558/13; 564/23, 26, 28, 29, 44, 48, 49, 53, 52, 54, 440, 442, 443

[56] References Cited
FOREIGN PATENT DOCUMENTS 762485 7/1967 Canada ..................... 564/442

*Primary Examiner*—Alan Rotman

[57] ABSTRACT

Dihalo and haloalkyl, haloalkoxy or haloalkylthio-substituted anilines and aniline derivatives, e.g. isocyanates that are useful in the preparation of acyl ureas having insecticidal activity.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

Claim 2 is determined to be patentable as amended.

Claims 3-5, dependent on an amended claim, are determined to be patentable.

2. [Compound of claim 1] *A compound having the formula*

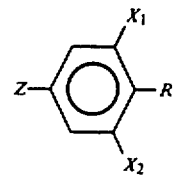

wherein $X_1$ and $X_2$ are independently F, Cl or Br, [and] R is $OCF_3$, $OCF_2CHCl_2$, $OCF_2CHF_2$, $OCF_2CHFCl$ or $OCF_2CHFBr$ *and Z is $NH_2$,*

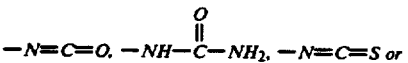

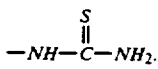

* * * * *